(12) United States Patent
Höfler et al.

(10) Patent No.: US 6,447,776 B1
(45) Date of Patent: *Sep. 10, 2002

(54) MUTATIONS OF E CADHERIN AS A BASIS FOR THE DIAGNOSIS AND THERAPY OF HUMAN MALIGNANT TUMORS

(75) Inventors: Heinz Höfler, München; Karl-Friedrich Becker, Garching bei München; Elisabeth Kremmer, Freising; Manfred Eulitz; Christoph Schuhmacher, both of München, all of (DE)

(73) Assignee: GSF Forschungszentrum fur Umwelt und Gesundheit GmbH

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/899,279

(22) Filed: Jul. 23, 1997

(30) Foreign Application Priority Data

Jul. 24, 1996 (DE) ......................... 196 29 938

(51) Int. Cl.[7] ..................... C07K 16/30; A61K 39/395; C12N 5/20
(52) U.S. Cl. ................ 424/156.1; 424/130.1; 424/138.1; 424/139.1; 424/141.1; 424/155.1; 435/326; 435/330; 435/331; 435/344; 435/344.1; 530/387.1; 530/387.7; 530/387.9; 530/388.1; 530/388.8; 530/388.85
(58) Field of Search ............ 424/130.1, 139.1, 424/138.1; 435/70.21, 326, 344; 530/387.1, 388.1

(56) References Cited

U.S. PATENT DOCUMENTS 5,610,281 A * 3/1997 Brenner et al.
5,652,115 A * 7/1997 Marks et al.
5,807,978 A * 9/1998 Kokolus et al.
5,821,328 A * 10/1998 King et al.

OTHER PUBLICATIONS

I. Kawanishi et al. Mol. Cell Biol. 15:1175–1181, (1995).*
Rosen et al. (Eds.) Dictionary of Immunology, Stockton Press, NY, 1989, p. 199.*
Aridor et al Nature Medicine 5:745–751 (1999).*
Kopito Physiological Reviews 79(Suppl No.: 1) S167–S173 (1999).*
Becker, K–F. et al., "Exon Skipping in the E–cadherin Gene Transcript in Metastatic Human Gastric Carcinomas," *Human Molecular Genetics* (1993) 2(6): 803–804.
Becker, K–F. et al., "Frequent Somatic Allelic Inactivation of the E–cadherin Gene in Gastric Carcinomas," *Journal of the National Cancer Institute*, (Jul. 19, 1995) 87(14): 1082–1084.
Becker, K–F. et al., "Single Nucleotide Polymorphisms in the Human E–cadherin Gene," *Hum. Gener.* (1995) 96: 739–740.
Becker, K–F. et al., "E–Cadherin Gene Mutations Provide Clues to Diffuse Type Gastric Carcinomas," *Cancer Research* (Jul. 15, 1994) 54: 3845–3852.

* cited by examiner

*Primary Examiner*—Phillip Gambel
(74) *Attorney, Agent, or Firm*—Townsend and Townsend and Crew

(57) ABSTRACT

The present invention describes monoclonal antibodies which are useful for the specific detection of diffuse gastric carcinoma. Further embodiments describe therapeutic and diagnostic means for the detection and for the therapy of diffuse gastric carcinomas.

3 Claims, 6 Drawing Sheets

Figure 1:
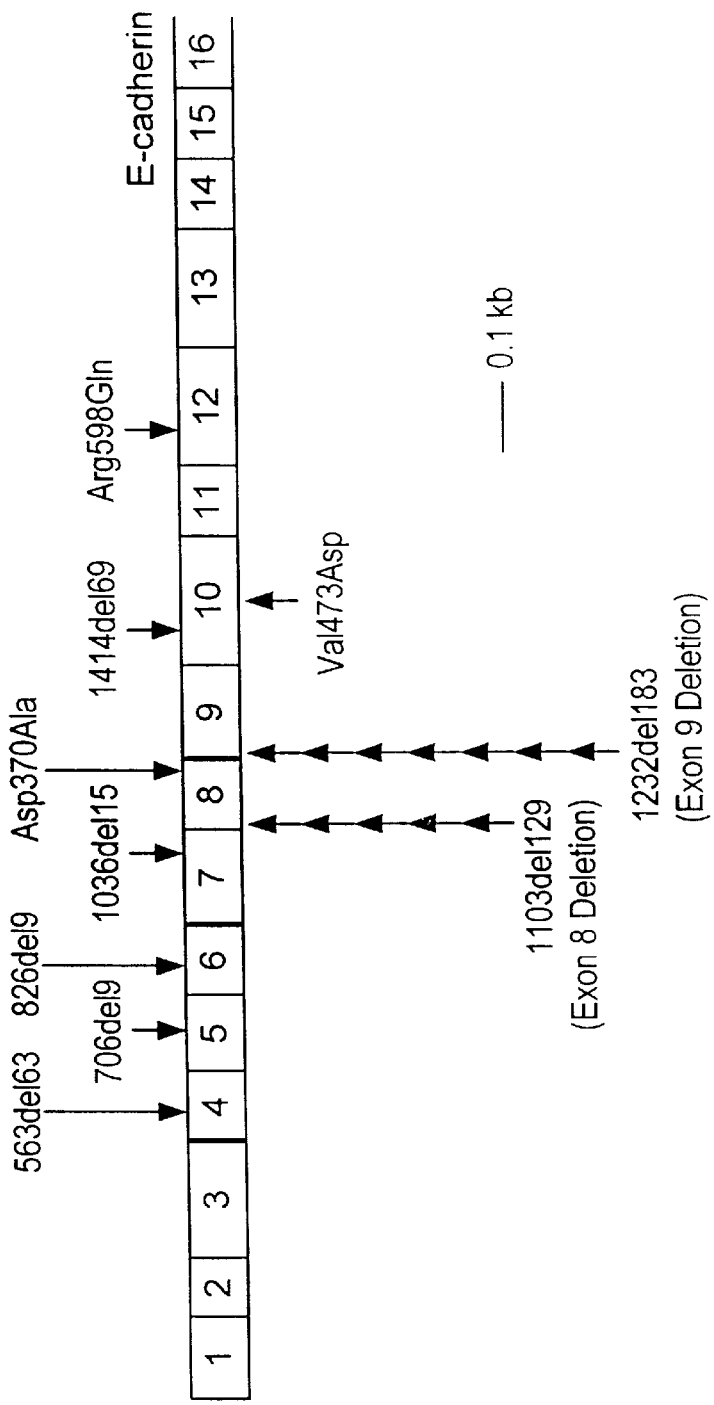

Immunofluorescence. Mutated E-cadherin protein (exon 9 deletion) can be detected at the cellular junctions (bright lines) of transfected cells (see text)

Immunoelectron microscopy. Mutated E-cadherin protein (arrows) can be detected at the membrane of transfected cells (see text)

Rapid diagnosis of E-cadherin.

Western blot using mutation specific E-cadherin antibody 7E6. In contrast to the not mutation-specific E-cadherin antibody HECD-1, the mutation-specific antibody 7E6 exclusively detects mutated E-cadherin protein. del9, exon 9 deleted E-cadherin; WT, wild-type; -, untransfected.

Immunohistochemistry using mutation-specific E-cadherin antibody 7E6. The mutation-specific antibody 7E6 exclusively detects tumour cells (arrows) of a diffuse-type gastric carcinoma. Non-tumourous glands (arrowheads) are not labeled.

MUTATIONS OF E CADHERIN AS A BASIS FOR THE DIAGNOSIS AND THERAPY OF HUMAN MALIGNANT TUMORS

CROSS REFERENCED TO RELATED APPLICATIONS

This application claims priority to DE application No. 196 29 938.1, filed on Jul. 24, 1996.

FEDERALLY SPONSORED RESEARCH OR DEVELOPMENT

Not Applicable

The invention relates to monoclonal antibodies specifically directed against mutated transmembrane E-cadherin and useful for the determination of gastric carcinomas.

BACKGROUND OF THE INVENTION

1. Field of the Invention

Introduction

2. Description of Related Art

Statistical evaluations of the causes of death show malignant tumors to be in a front position worldwide. Among these tumors the gastric carcinoma internationally takes the second position of tumors resulting in death. Several genetic alterations have been reported in association with the gastric carcinoma including microsatellite instabilities and alterations of the genes p53, APC DCC (Tahara E: Genetic alterations in human gastrointestinal cancers. Cancer 1995; 75:1410–1417). Histomorphologically, two types of gastric carcinoma can be distinguished (Laurén P: The two histological main types of gastric carcinoma: diffuse and so-called intestinal-type of carcinoma. Acta Pathol. Microbiol. Scand. 1965; 64:31–49): one type are the intestinal carcinomas having a glandular differentiation, the other type consists of diffuse carcinomas with disrupted tissue architecture. So far, the genetic basis for this bipartite development and morphology has not been clarified. Possibly, alterations in the E-cadherin molecule may be of importance in this respect. E-cadherin is a homophilic transmembrane cellular adhesion molecule playing a key role in the interaction of epithelial tissues. Initial molecular-biological studies of the E-cadherin gene comprising 16 exons indicated that mutations may contribute to the morphology and growth type of gastric carcinomas (Becker K-F, Atkinson M J, Reich U, Becker I, Nekarda H, Siewert J R, Höfler H: E-cadherin gene mutations provide clues to diffuse type gastric carcinomas. Cancer Res. 1994; 54(14):3845–3852).

Basically, alterations of malignant tumors are of interest for the explanation of certain biological patterns of behaviour; these phenomenons may be used as a specific characteristic feature and, therefore, as a tumor marker. These characteristics include cellular products and also typical properties of the cell surface which can be assessed in a direct or indirect manner. To date, the isolation of a surface antigen or cellular product restricted solely to tumor cells has not been successful. Up to now the increased occurrence of certain cellular properties (surface antigen, intracellular proteins, secreted cellular products) in the body relative to normal tissue has been used as the basis for diagnosis and therapy of malignant diseases.

State of the use of E-cadherin in Diagnosis and Therapy

The first publications reported that E-cadherin—detected by immunohistochemistry using specific antibodies—showed an altered expression pattern in tumor cells. The immunoreactivity of E-cadherin was partly reduced in or absent from tumor tissue (see Table 1). Other authors thought this fact to be the reason for a decreased production ("downregulation") of the protein in the tumor (cf. Birchmeier, DE-A-41 10 405 A1).

TABLE 1

E-cadherin immunoreactivity in patients suffering from gastric carcinoma

| Histology | n[a] | E-cadherin immunoreactivity | | Reference |
| --- | --- | --- | --- | --- |
| | | unchanged[b] | abnormal[c] | |
| diffuse | 28 | 13 (46%) | 15 (54%) | 1 |
| intestinal | 93 | 69 (74%) | 24 (26%) | 1 |
| diffuse | 14 | 7 (50%) | 7 (50%) | 2 |
| intestinal | 22 | 21 (95%) | 1 (5%) | 2 |
| diffuse | 11 | 6 (55%) | 5 (45%) | 3 |
| diffuse | 21 | 0 | 21 (100%) | 4 |
| intestinal | 30 | 5 (17%) | 25 (83%) | 4 |
| diffuse | 27 | 19 (70%) | 8 (30%) | 5 |
| intestinal | 17 | 17 (100%) | 0 | 5 |

Legend of Table 1:
[a]Number of patients examined;
[b]immunoreactivity of E-cadherin similar to "normal" tissue;
[c]E-cadherin immunoreactivity in the tumour decreased or not present.
References for Table 1.
1 Shino Y, Watanabe A, Yamada Y, Tanase M, Yamada T, Matsuda M, Yamashita J, Tatsumi M, Miwa T, Nakano H: Clinicopathologic evaluation of immunohistochemical E-cadherin Expression in human gastric carcinomas. Cancer 1995; 76:2193–2201.
2 Brito MJ, Jacinto L, Jankowski J, Pignatelli M, Filipe MI: E-cadherin (cell adhesion molecule) in gastric carcinoma. Path. Res. Pract. 1995; 191:628 [Abstract].
3 Matsui S, Shiozaki H, Inoue M, Tamura S, Doki Y, Kadowaki T, Iwazawa T, Shimaya K, Nagafuchi A, Tsukita S, Mori T: Immunohistochemical evaluation of alpha-catenin expression in human gastric cancer. Virchows Archiv 1994; 424:375–381.
4 Mayer B, Johnson JP, Leitl F, Jauch KW, Heiss MM, Schildberg FW, Birchmeier W, Funke I: E-cadherin expression in primary and metastatic gastric cancer: down-regulation correlates with cellular dedifferentiation and glandular disintegration. Cancer Res. 1993; 53:1690–1695.
5 Shimoyama Y, Hirohashi S: Expression of E- and P-cadherin in gastric carcinomas. Cancer Res. 1991; 51(8):2185–2192.

Our own considerations regarding these phenomena aimed for the first time at the integrity of the E-cadherin gene. After RNA extraction, reverse transcription and direct DNA sequencing, the molecular-biological examination of gastric carcinoma tissue revealed defects in the E-cadherin gene. Gastric carcinomas of the diffuse subtype were examined for genetic alterations in a part of the E-cadherin gene (exons 6–10 and 13–16). Loss of exons 8 and 9, partial loss of exon 10, or a point mutation in the region of exon 8 were observed (Becker K-F, Atkinson M J, Reich U, Becker I, Nekarda H, Siewert J R, Höfler H: E-cadherin gene mutations provide clues to diffuse type gastric carcinomas. Cancer Res. 1994; 54(14):3845–3852). Tumors of the intestinal subtype showed no mutations leading to structural alterations. Analysis of the found mutations revealed that individual deletions occurred with somewhat higher frequency, but also point mutations or smaller deletions could be observed. Immunohistochemical staining (antibody: HECD-1, Takara Biomedicals, Japan, cf. methodology section) of some of the cases with mutated E-cadherin predominantly showed a transmembrane staining of the tumor cells and also staining of non-tumorous-mucosa. We were not able to distinguish whether the labeling of the tumor cells corresponded to the detection of wildtype E-cadherin or mutated E-cadherin. On the one hand, there was the possibility that mutated protein continued to be incorporated into the cellular membrane and that the antibody against E-cadherin (HECD-1) recognizes an epitope apart from the mutated region. A further explanation could be the binding of the antibody to wildtype E-cadherin which—being generated by the second, not mutated allele—is also expressed in tumor cells. Initially, the fact that some of the tumors showed no staining led us to suggest the presence of further mutations apart from the examined exons 6–10 and 13–16 which might have an influence on the translation or the stability of the protein.

It is an object of the present invention to provide monoclonal antibodies which are specifically suitable for the detection of gastric carcinomas and in particular diffuse gastric carcinomas.

SUMMARY OF THE INVENTION

This object is achieved according to the invention by the monoclonal antibodies characterized in more detail in claim 1. Preferred embodiments of the invention follow from the dependent as well as the secondary claims.

The analysis of regions of the E-cadherin gene which have not been examined so far (exons 1–5, 11, and 12), and the sequencing of the cDNA of E-cadherin of ten additional cases of diffuse gastric carcinoma revealed further mutations in diffuse gastric carcinoma (cf. the "Methodology" section). These newly found mutations (Table 2) surprisingly continued to show a typical pattern. In all of the cases, these mutations were either multimers of a base triplet not affecting the reading frame or they were point mutations. By these studies we were able to exclude the suggestion made after immunohistochemical examination that the loss of the immunoreactivity may be caused by translation-disrupting mutations. In parallel to the examination of gastric carcinomas also other epithelial tumors were analysed. None of the cases of mamma carcinoma, oesophagus carcinoma, and large intestinal carcinoma showed patterns corresponding to those of gastric carcinoma.

TABLE 2

E-cadherin mutations in gastric carcinoma found by us.

| Mutation | Exon | Nucleotide position | Amino Acid(s) | Type of mutation |
| --- | --- | --- | --- | --- |
| 563del63 | 4 | 563 | Amino acids 157–177 | in-frame deletion of 63 bp |
| 706del9 | 5 | 706 | 205–207 | in-frame deletion of 9 bp |
| 826del9 | 6 | 826 (T to G) | 245–247; 244 (Asp to Glu) | in-frame deletion of 9 bp and missense mutation |
| 1036del15 | 7 | 1036 | 315–319 | in-frame deletion of 15 bp |
| 1103del129 | 8 | 1103 | 337–379 | in-frame deletion of 129 bp (complete loss of exon 8) |
| Asp370Ala | 8 | 1203 | 370 (Asp to Ala) | Missense mutation |
| 1232del183 | 9 | 1232 | 380–440 | in-frame deletion of 183 bp (complete loss of exon 9) |

TABLE 2-continued

E-cadherin mutations in gastric carcinoma found by us.

| Mutation | Exon | Nucleotide position | Amino Acid(s) | Type of mutation |
| --- | --- | --- | --- | --- |
| 1414del69 | 10 | 1414 | 441–463 | in-frame deletion of 69 bp |
| Val473Asp | 10 | 1512 | 473 (Val to Asp) | Missense mutation |
| Arg598Gln | 12 | 1887 | 598 (Arg to Gln) | Missense mutation |

Additional studies carried out with respect to the characteristics of the mutations as well as sequencing of additional tumors now have led to a principle which has not yet been reported and is unique in the case of carcinomas: the alterations of E-cadherin in diffuse gastric carcinoma are in-frame mutations (and not disruptions of the reading frame). This result is useful for diagnostic and therapeutic purposes.

Figure 2:
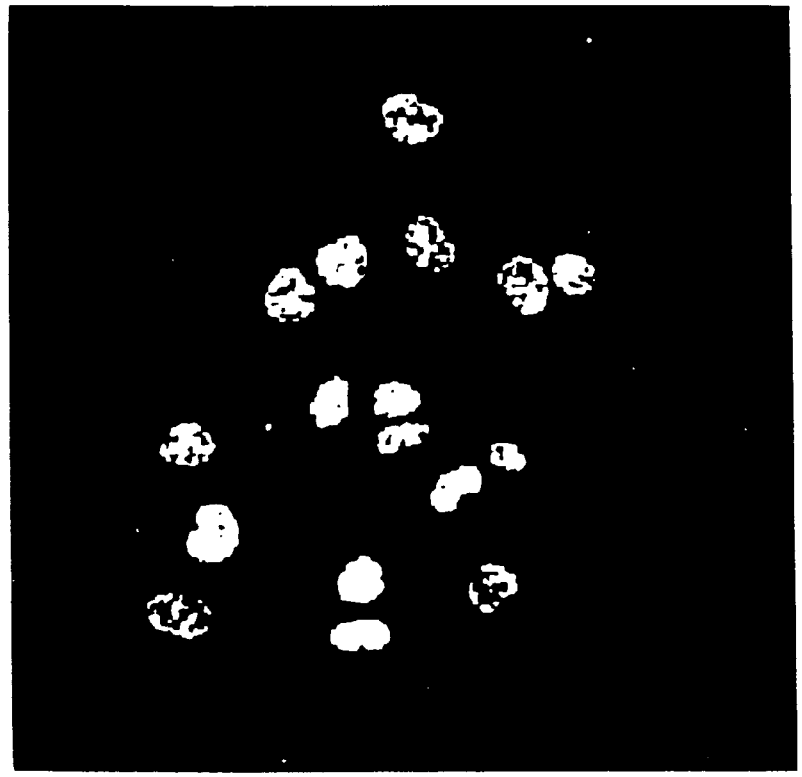
Figure 3:
Figure 4:
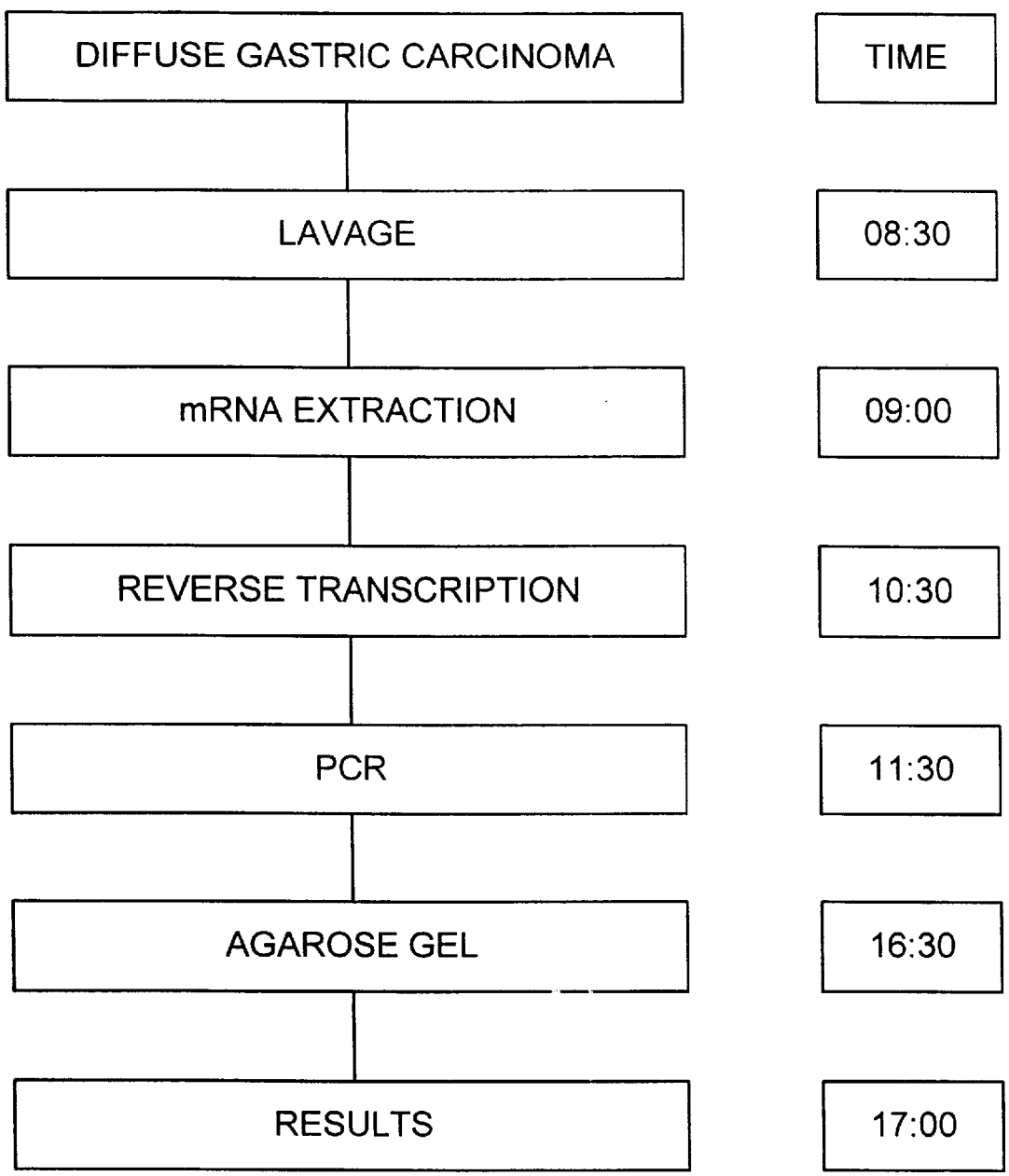
Figure 5:
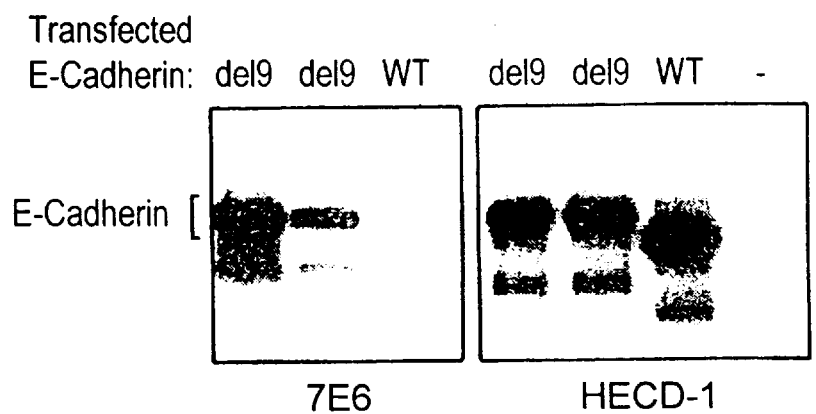
Figure 6:

The invention will in the following be explained in more detail with respect to the Figures. The Figures show:

FIG. 1 a review of the E-cadherin mutations in diffuse gastric carcinoma known so far which typically represent in-frame deletions;

FIG. 2 the determination of the membraneous localisation of mutated E-cadherin by immunofluorescence;

FIG. 3 the determination of the membraneous localisation of mutated E-cadherin by immunoelectron microscopy;

FIG. 4 a flow diagram of the rapid diagnosis of E-cadherin mutations according to the invention;

FIG. 5 Western blot stained by mutation-specific E-cadherin antibody 7E6;

FIG. 6 immunohistochemistry stained by mutation-specific E-cadherin antibody 7E6.

DETAILED DESCRIPTION OF THE INVENTION

We have been successful in providing evidence for a typical form of mutation—in-frame mutations (deletions of multimers of a base triplet or point mutations, respectively)—in the case of the diffuse gastric carcinoma (see FIG. 1).

These characteristic mutations enable as to conclude that an altered protein is generated in all of the cases and is further expressed by the cell. Evidence for this suggestion has been gained by transfection of the mutated genes into a cell line deficient for E-cadherin (MDA mamma carcinoma cells) (see Annex for methodology). Stably transfected cells expressed the mutated protein at the cellular membrane; the membraneous localization of the mutated protein has been unequivocally proven by means of immunofluorescence (FIG. 2) and electron microscopy (FIG. 3) using the exon 9 deletion as an example. The undisturbed membraneous localization of the mutated protein is of critical importance for its further use in diagnosis and therapy.

The loss of base sequences or the presence of point mutations, respectively, generate a new, unique and unmistakable RNA sequence while the continuity of transcription is maintained. This "mistake" is then anchored in the protein by an altered amino acid sequence in the course of the subsequent translation. The new protein sequences generated by the mutation are listed in detail in Table 3.

Individual tumor cells are unmistakably labeled by these sequences, i.e. by their mutated E-cadherin gene. A search (comparison of homology) carried out in several gene data banks (via EMBL/GenBank/SWISS-PROT/PDB, Release 32.0) provided no similarity to any sequences known up to now. Early gastric carcinomas were examined with regard to the clonality of the mutation event. Since also in these cases mutations could be detected (own observations) mutations in E-cadherin must be an early event in the course of tumor development, possibly going back to the original malignant clone.

we attempted to produce examparily a monoclonal antibody against the shortened transmembrane protein via the newly generated sequence using the exon 9 deletion as an example (see Annex for methodology). In this case it was not clear whether the mutated region would be suitable as an antigenic determinant since the sterical arrangement of this epitope is unknown. 23 hybridomas (antibody-producing clones) were generated, and their specificity was tested in vitro (see Annex). One clone (7E6-1) was found which

TABLE 3

Newly generated E-cadherin protein sequences by mutations

| Mutation | "Normal" E-cadherin sequence | SEQ ID No. | New E-cadherin sequence | SEQ ID No. |
|---|---|---|---|---|
| 563del63 | PGLRRQKRDW/VIPPISCPEN | 1 | PGLRRQKRDW/IKSNKDKEGK | 2 |
| 706del9 | QGADTPPVGV/FIIERETGWL | 3 | QGADTPPVGV/ERETGWLKVT | 4 |
| 1036del115 | LSQDPELPDK/NMFTINRNTG | 5 | LSQDPELPDK/NRNTGVISVV | 6 |
| 1103del129 | SVVTTGLDRE/SFPTYTLVVQ | 7 | SVVTTGLDRE/YKGQVPENEA | 8 |
| 1232del183 | DNPPIFNPTT/YKGQVPENEA | 9 | DNPPIFNPTT/GLDFEAKQQY | 10 |
| 1414del69 | NNDGILKTAK/GLDFEAKQQY | 11 | NNDGILKTAK/VSLTTSTATV | 12 |
| Asp370Ala | TAVITVTDTNDNPPIFNPTT | 13 | TAVITVTDTNANPPIFNPTT | 14 |
| Val473Asp | EVSLTTSTATVTVDVLDVNE | 15 | EVSLTTSTATDTVDVLDVNE | 16 |
| Arg598Gln | VNDNAPIPEPRTIFFCERNP | 17 | VNDNAPIPEPQTIFFCERNP | 18 |
| 826del9 | AVSSNGNAVED/PMEILITV | 19 | AVSSNGNAVEE/ILITVTDQN | 20 |

The dash (/) shows the position of a deletion; the protein sequence is altered starting from this position; underlined and bold letters indicate amino acids changed by point mutations.

The E-cadherin mutations shown in Table 3 as well as further yet unknown mutations can be used for diagnostic and therapeutic purposes for example as follows:

Rapid RNA Extraction and subsequent Detection of the Mutation by PCR:

The characteristic feature of the mutations described (mainly deletions!) is excellently suitable for a rapid specific test: the amplification of a section of the cDNA by suitable primers (see methodology) embracing the mutated exon regions—in combination with a rapid RNA extraction (see methodology)—allow for the clinical utilization of the invention (time factor!). The detection in this case can be performed on tissues (e.g. biopsies, punctates, cytologies) and body fluids (e.g. blood).

As an example, biopsies and peritoneal lavages of gastric carcinoma patients were examined for mutations of the E-cadherin gene. Within 8 hours (see FIG. 4) it is possible to specifically determine an alteration in E-cadherin and thereby to provide in-time information for clinical problems. Hereby, seen in the context of the further explanations (see antibodies/therapy) it will be possible to rapidly affect a treatment plan. Basically, this methodology may also be used for the specific initial detection of a gastric carcinoma. Also, it is possible to use it in differential diagnosis (e.g. biopsy of metastases) of other malignomas in the case of an unknown primary tumor (e.g. mamma carcinomas).

Antibodies

The combination of the membraneous localisation and the tumor specificity of the mutated E-cadherin protein allowed for the first time the specific production of a monoclonal antibody exclusively directed against tumor cells.

By the tumor-specific gene sequences provided by the invention it is possible for the first time to detect amino acids the sequence of which stands for a corresponding protein being restricted exclusively to tumor cells. By this, it is possible to generate antibodies selectively directed against the mutated region of E-cadherin. To verify this hypothesis, recognizes exon 9-deleted E-cadherin protein on a Western blot and by immunofluorescence. 7E6 antibody fails to detect "normal" E-cadherin (FIG. 5). This cell line producing the 7E6 antibody has been deposited at the DSM (Deposit No. DSM ACC 2277) (Reference Mark: delta CAD-9, clone 7E6-1). The date of deposit was Jun. 27, 1996, and the name and address of the depository are DSMZ-Deutsch Sammlung Von Mikroorganismen und Zellkulturen GmbH, Mascheroder Weg 1b, D-38124, Braunschweig, Germany. The 7E6 antibody recognizes the mutation 1232del183.

It could not be expected that this antibody would be functional with regard to material fixed in formalin and embedded in paraffin. For the first time, this allowed for the specific detection of tumor cells on a histological section by means of immunohistochemical methods (FIG. 6). Non-tumorous cells on the same section were not labeled! Thereby, it has become possible to assign the mutated molecule to individual cells. According to our knowledge, a tumor marker with comparable specificity has not yet been described.

The hybridoma cell line deposited at the DSM under the deposit No. ACC 2277 represents merely an example for a cell line producing the monoclonal antibodies provided by the invention. According to the invention, additional antibodies have been already produced which recognize the in-frame mutations. To provide these antibodies is well within the skills of a person skilled in the art working in this field. The 7E6 monoclonal antibody as well as any other antibody generated specifically directed against E-cadherin mutations can be used in diagnosis and therapy as described in the following.

Diagnostics using Mutation-specific E-cadherin Antibodies

Retrospective examination of formalin-fixed and paraffin-embedded tissue regarding defects in E-cadherin by means of immunohistochemistry.

Prospective in vitro examination of:

Blood for the detection of circulating tumor cells
    as a basic screening for diffuse gastric CA for the evaluation of the pre-, intra-, and post-operative dissemination of tumor cells as possible markers for the course of the disease.

Tumor biopsy
  for the pre-therapeutic detection of mutated E-cadherin with regard to a plan for a pre-operative (neoadjuvant), intra-operative (peritoneum, portal vein) and post-operative (additive or adjuvant) therapy.
OP preparation
  for the determination of-tumor cells (e.g. edge of removal, ensuring the extent of resection)
Lymph nodes
  for the detection of metastases and tumor cells ("microenvolvement")
Lavage
  for the determination of disseminated tumor cells in the peritoneal cavity
Tissue
  for the determination of disseminated tumor cells (immunohistochemistry)
Differential diagnosis of carcinomas
  immunohistochemical determination of characteristic E-cadherin mutations for differential diagnostic evaluation of suspected tissue samples
Screening of high-risk groups ("cancer families") determination of E-cadherin mutations in blood cells (DNA)
in vivo
  Prerequisite: humanization of the antibody for therapeutic use specific determination of tumor cells by immunoscintigraphy:
    pre-therapeutically for set up of operation plan/therapy plan
    for the control of the course of therapy or, respectively, for the verification of a successful therapy and for the control of the post-therapeutical course of the disease
  Therapy by mutation-specific E-cadherin antibodies:
    immunoradiotherapy
      coupling of a source of radiation to the mutation-specific antibody
    immunotoxin therapy
      coupling of a toxin (e.g. pseudomonas toxin) to the antibody
  Somatic gene therapy by mutation-specific E-cadherin antibodies:
    possible ways for a specific gene transfer:
      coupling to viral gene expression systems (e.g. adenovirus, or MVA, vaccinia-derived expression vectors);
      coupling to non-viral gene expression systems (e.g. T7 RNA polymerase+T7 DNA vector);
    Possible therapy approach using genetic engineering:
      incorporation of cofactors (e.g. B7) to label the tumor cells for the endogenous immune system;
      incorporation of alloantigens (foreign HLA antigens, "major antigens") to activate the endogenous T cells and initiate an immune reaction against tumor cells having mutated E-cadherin "minor antigen");
      killing of tumor cells by specific incorporation of factors inducing apoptosis (e.g. p53); conversion of the malignant phenotype by specific incorporation of wildtype oncogenes/suppressor genes (e.g. E-cadherin itself); activation of a protoxin to form a toxin by specific inclusion of an enzyme (e.g. cytosin deaminase, conversion of 5-fluoro cytosin into the toxic 5-fluoro uracil);
  Ribozymes
    e.g. site-specific destruction of the RNA coding for the multidrug-resistance transporter Further examples showing fields of use of the E-cadherin mutations
  bone marrow purching:
    specific determination of tumor cells in treated bone marrow in vitro and concurrent use of the antibody for specific elimination of tumor cells from the bone marrow (e.g. by a toxin bound to the antibody);
  immune therapy
    charging of dendritic cells with mutated E-cadherin peptide sequences (see Table 3) for antigen presentation (activation of T cell clones specifically directed against tumor cells).

The intracellular degeneration of proteins generates peptides having different lengths. Peptides with a length of 9–11 amino acids are "checked" by the MHC of the cell (the binding capacity in the peptide binding region depends on a particular arrangement of the individual amino acids and distinguishes between "nonself" and "self") and are presented at the cell surface if a particular sequence has been recognized as nonself. By the action of costimulators, this can lead to an immune reaction. For the peptide sequences of the mutated E-cadherin described for the first time by us and other peptides being generated by mutations, it can be expected that some of them will be presented by the MHC as nonself peptides. The fact that this event fails to stimulate an immune reaction in patients may be explained by the property of tumor-cells to present antigens poorly. The mutation-spanning peptides found can be mounted—in varying lengths—on professional, antigen presenting cells (dendritic cells). Due to the presence of all neccessary costimulators on this cells a corresponding T cell stimulation against such MHC-peptide complexes is achieved. In this way, also the tumor cells which initially have been ignored by the immune system are then recognized as nonself and are eliminated.

This use does not require a particular mutation-specific antibody, however, it requires knowledge about the newly generated peptide sequences described according to the invention.

According to the invention, also the following objects and methods are comprised:

monoclonal antibody specifically directed against such amino acid sequences of mutated E-cadherin which have been generated by in-frame mutations on the DNA level and a. lead to the loss of at least one base triplet or a multimer thereof in an exon on the RNA level and subsequently lead to the deletion of at least one amino acid of the wt E-cadherin protein, and/or b. lead to the exchange of one or two nucleotides of at least one base triplet in an exon on the RNA level and subsequently to the exchange of at least one amino acid of the wt E-cadherin protein.

Monoclonal antibody directed against such sequences of mutated E-cadherin which have been generated by in-frame mutations on the DNA level and lead to the loss of at least one base triplet or a multimer thereof in exon 8, exon 9, or exon 10 on the RNA level.

Monoclonal antibody recognizing at least the sequence region among one or more of the following amino acid sequences which has been generated by deletion or amino acid exchange as compared to E-cadherin, selected from at least one sequence of the following group:

| Mutation | Mutated E-cadherin sequence | SEQ ID NO: |
|---|---|---|
| 563de163 | PGLRRQKRDW/IKSNKDKEGK | 2 |
| 706de19 | QGADTPPVGV/ERETGWLKVT | 4 |
| 1036de115 | LSQDPELPDK/NRNTGVISVV | 6 |
| 1103de1129 | SVVTTGLDRE/YKGQVPENEA | 8 |
| 1232de1183 | DNPPIFNPTT/GLDFEAKQQY | 10 |
| 1414de169 | NNDGILKTAK/VSLTTSTATV | 12 |
| Asp370Ala | TAVITVTDTNANPPIFNPTT | 14 |
| Val473Asp | EVSLTTSTATDTVDVLDVNE | 16 |
| Arg598Gln | VNDNAPIPEPQTIFFCERNP | 18 |
| 826de19 | AVSSNGNAVEE/ILITVTDQN | 20 | wherein "/" denotes the position of a deletion, and underlined and bold letters denote amino acids changed by point mutations, respectively, each in comparison to the wt E-cadherin protein.

The invention also comprises a mixture of at least two of the above mentioned monoclonal antibodies.

The invention comprises in particular monoclonal antibodies as those described above which are specifically directed against the amino acid sequences of mutated transmembrane E-cadherin.

A further embodiment of the invention comprises an immune test for the detection of gastric carcinoma cells comprising at least one monoclonal antibody of the present invention.

Furthermore, the invention comprises the following embodiments:

Primers for PCR processes for the amplification of DNA and cDNA sequences of mutated exon regions of E-cadherin selected to specifically comprise the mutated sequences generated by in-frame mutations on the DNA level which a. lead to the loss of at least one base triplet or a multimer thereof in an exon on the RNA level and subsequently lead to the deletion of at least one amino acid of the wt E-cadherin protein, and/or b. lead to the exchange of one or two nucleotides of at least one base triplet in an exon on the RNA level and subsequently to the exchange of at least one amino acid of the wt E-cadherin protein.

Primers for PCR processes for the amplification of DNA and cDNA sequences of mutated exon regions of E-cadherin selected to specifically comprise the mutated sequences and selected from at least one primer of the following group:

| Primer name | Sequence | SEQ ID NO: |
|---|---|---|
| ATG | 5'-ATGGGCCCTT GGAGCCG | 21 |
| Ex 8 | 5'-CTAGGTATACC CTGGTGG | 22 |
| Ex9/1 | 5'-TACAAGGGTC AGGTGCCTGAG | 23 |
| rEx 10 | 5'-GGGGGCTTCAT TCACATC | 24 |
| r3'/2/neu | 5'-CCAGCACATG GGTCTGGG | 25 |
| Ex7 | 5'-ACCTCTGTGAT GGAGGTC | 26 |
| rEx11 | 5'-TGTGTACGTGC TGTTCTTCACGTG | 27 |

| Name and sequence of the "forward" primer | Name and sequence of the "reverse" primer |
|---|---|
| ATG; 5'-CCATGGGCCCT TGGAGCCGC (SEQ ID NO:28) | rEx6; 5'-CTGGAAGAGCA CCTTCCATGAC (SEQ ID NO:29) |
| Ex5; 5'-ACAGAGCCTCTG GATAGAGAACGC (SEQ ID NO:30) | rEx10/2; 5'-CCACATTCGT CACTGCTACG (SEQ ID NO:31) |
| Ex9/2a; 5'-GTGTCCGAGG GGCTGTATACAC (SEQ ID NO:32) | rEx11; 5'-TGTGTACGTGC TGTTCTTCAC (SEQ ID NO:33) |
| Ex10/2; 5'-GTGTCCGAGG ACTTTGGCGTG (SEQ ID NO:34) | rEx13; 5'-TCAGAATTAGC AAAGCAAGAATTCC (SEQ ID NO:35) |
| Ex13; 5'-GGCGTCTGTAG GAAGGCACAG (SEQ ID NO:36) | r3prime; 5'-CCAGCACATG GGTCTGGG (SEQ ID NO:37) |

It is particularly preferred that the invention comprises therapeutic or diagnostic means containing as an effective substance at least one nucleic acid which specifically hybridizes to the DNA or cDNA or to RNA sequences derived therefrom of mutated E-cadherin wherein the DNA or cDNA exhibits in-frame mutations which a. lead to the loss of at least one base triplet or a multimer thereof in an exon on the RNA level and subsequently lead to the deletion of at least one amino acid of the wt E-cadherin protein, and/or b. lead to the exchange of one or two nucleotides of at least one base triplet in an exon on the RNA level and subsequently to the exchange of at least one amino acid of the wt E-cadherin protein.

Furthermore, the invention comprises therapeutic or diagnostic means containing a nucleic acid which hybridizes to at least some of the following DNA sequences or complementary strands thereof or RNA sequences derived therefrom under stringent conditions wherein also at least the sequence region generated by in-frame mutation is included:

Mutation 563del63: CCT GGC CTC AGA AGA CAG AAG AGA GAC TGG / ATC AAA TCC AAC AAA GAC AAA GAA GGC AAG (SEQ ID No: 38)

Mutation 706del9: CAA GGA GCT GAC ACA CCC CCT GTT GGT GT / T GAA AGA GAA ACA GGA TGG CTG AAG GTG ACA (SEQ ID NO: 39)

Mutation 1036del15: CTC AGC CAA GAT CCT GAG CTC CCT GAC AAA / AAC AGG AAC ACA GGA GTC ATC AGT GTG GTC (SEQ ID NO:40)

Mutation 1103del1129: AGT GTG GTC ACC ACT GGG CTG GAC CGA GAG / TAC AAG GGT CAG GTG CCT GAG AAC GAG GCT (SEQ ID NO: 41)

Mutation 1232del183: GAT AAT CCT CCG ATC TTC AAT CCC ACC ACG / GGC TTG GAT TTT GAG GCC AAG CAG CAG TAC (SEQ ID NO: 42)

Mutation 1414del69: AAC AAC GAT GGC ATT TTG AAA ACA GCA AAG GTN / TCT CTC ACC ACC TCC ACA GCC ACC GTC (SEQ ID NO: 43)

Mutation Asp370Ala: ACA GCT GTG ATC ACA GTC ACT GAC ACC AAC GCT AAT CCT CCG ATC TTC AAT CCC ACC ACG (SEQ ID NO: 44)

Mutation Val473Asp: GAG GTC TCT CTC ACC ACC TCC ACA GCC ACC GAC ACC GTG GAT GTG CTG GAT GTG AAT GAA (SEQ ID NO: 45)

Mutation Arg598Gln: GTG AAT GAC AAC GCC CCC ATA CCA GAA CCT CAA ACT ATA TTC TTC TGT GAG AGG AAT CCA (SEQ ID NO: 46)

Mutation 826del9: GCT GTG TCA TCC AAC GGG AAT GCA GTT GAG GA / G ATT TTG ATC ACG GTA ACC GAT CAG AAT (SEQ ID NO: 47)

Moreover, according to the invention there are also comprised therapeutic or diagnostic means containing as an effective substance a nucleic acid which hybridizes to the above mentioned nucleic acid under stringent conditions.

Stringent conditions in the spirit of the present invention are defined as conditions which allow for selective and detectable specific binding of the nucleic acid to the nucleic acid defined according to the invention. A hybridization of this kind under stringent conditions preferably means a hybridization carried out at 68° C. in aqueous solution or at 42° C. in 50% formamide and subsequent washing of the filter at a temperature of 65° C. in an aqueous solution after which binding of the probe to the nucleic acid defined according to the invention or to the RNA derived therefrom can still be detected. If neccessary, also less severe hybridization and/or washing conditions may be used.

The monoclonal antibodies provided according to the invention are useful in diagnosis and therapy of gastric carcinomas and in particular of diffuse gastric carcinoma.

For therapy, the monoclonal antibodies of the invention may for example be bound to a means for selective elimination of at least some of the gastric carcinoma cells. This means may preferably include a toxin or a source of radiation.

The present invention also comprises the DNA oligonucleotides and the oligopeptides characterized in more detail in the claims. These are useful for immunotherapy of tumors, especially of gastric carcinomas.

frozen in liquid nitrogen. Total RNA of the deep-frozen tissue samples was isolated using standard procedures (guanidinium isothiocyanate extraction and CsCl centrifugation). Following reverse transcription of two μg of RNA the whole coding region of the E-cadherin cDNA was amplified by PCR. The PCR primers used are listed in Table 4. The amplification conditions for all of the PCR reactions were as follows: 1 min denaturation at 94° C.; 1 min primer annealing at 55° C.; and 1 min elongation at 72° C. Taq polymerase and amplification buffer (1.5 mM $MgCl_2$) were obtained from Perkin Elmer Corp., Foster City, Calif., USA. A Biomed PCR device (Biomed-Labordiagnostik, Oberschleißheim) was used. The products of the amplification were checked by agarose gel electrophoresis, and were subsequently purified using glass milk (GeneClean II, Bio101 Inc., La Jolla, Calif., USA). Afterwards, the full lengths of the isolated DNA amplificates were sequenced (Sequenase Version 2.0/USB, Cleveland, Ohio, USA).

TABLE 4

E-cadherin cDNA primers for PCR amplification of the complete coding sequence.

| Name and sequence of the "forward" primer | Name and sequence of the "reverse" primer | Nucleotide position[a] and length of the PCR product |
|---|---|---|
| ATG; 5'-CCATGGGCCCT TGGAGCCGC (SEQ ID NO:28) | rEx6; 5'-CTGGAAGAG- CA CCTTCCATGAC (SEQ ID NO:29) | 93–926; 834 bp |
| Ex5; 5'- ACAGAGCCTCTG GATA- GAGAACGC (SEQ ID NO:30) | rEx10/2; 5'- CCACATTCGT CACTGCTACG (SEQ ID NO:31) | 743–1472; 730 bp |
| Ex9/2a; 5'- CAGCGTGGGA GGCTGTATACAC (SEQ ID NO:32) | rEx11; 5'- TGTGTACGTGC TGTTCTTCAC (SEQ ID NO:33) | 1314–1780; 467 bp |
| Ex10/2; 5'- GTGTCCGAGG ACTTTGGCGTG (SEQ ID NO:34) | rEx13; 5'- TCAGAATTAGC AAAG- CAAGAATTCC (SEQ ID NO:35) | 1577–2264; 688 bp |
| Ex13; 5'- GGCGTCTGTAG GAAGGCACAG (SEQ ID NO:36) | r3prime; 5'- CCAGCACATG GGTCTGGG (SEQ ID NO:37) | 2171–2781; 611 bp |

[a]Nucleotide positions refer to an E-cadherin sequence available in the EMBL/GenBank data banks, Access No. Z13009.

In a further embodiment of the invention, there is described a process for the determination of tumor cells in a sample material containing human cells by the following steps of:
a. providing sample material containing human cells;
b. recovery of the mRNA from the human cells;
c. reverse transcription of the mRNA;
d. performing a polymerase chain reaction;
e. separating and analyzing the reaction products of the polymerase chain reaction.

The invention also comprises vectors containing the oligonucleotide sequences provided according to the invention.

Thus, it has been discovered by the invention that in-frame mutations of E-cadherin may be used in diagnosis and therapy of gastric carcinomas. The term "in-frame mutations" is intended to mean mutations or deletions in E-cadherin taking place on the DNA level which lead to a deletion or an base exchange on the RNA level while neither the deletion nor the mutation leads to a reading frame displacement.

Methodology
1. Search for New E-cadherin Mutations

Tissue of 63 patients suffering from gastric carcinoma was examined. Fresh tumor tissue after resection was deep- 2. Immunohistochemical Examination (Not Mutation-specific)

Archive material of tissue fixed in formalin and embedded in paraffin was subjected to deparaffinization and rehydration. Following treatment with citric acid and microwaves, the tissue samples were incubated for 15 minutes in 1% $H_2O_2$ to block endogenous peroxidase. For the determination of E-cadherin-specific immunoreactivity the tissues were incubated for 16 hours at 4° C. with the monoclonal antibody HECD-1 (Takara Biomedicals, Japan, 1:500 dilution). Visualization of antibody binding was carried out using the avidin-biotin complex (ABC) and the peroxidase method (ABC Elite Kit, Vector, Burlingame, Calif.; Sigma Fast DAB, Sigma, Deisenhofen). Hemalum was used for counterstaining of the nucleus. All of the tumor sections also showed portions of non-malignant mucosa as a control. Negative controls were performed by substituting the HECD-1 antibody by phosphate-buffered NaCl.

3. Cloning of E-cadherin Into Expression Vectors

To examinate the intracellular localisation of mutated E-cadherin the mutated molecules were cloned into expression vectors. As an example, 4 different mutants of E-cadherin mRNA in addition to human wild-type E-cadherin were cloned into expression vectors. Two of these 4 mutations exhibited a complete loss of one of the exons, either a deletion of exon 8 (129 bp) or a deletion of exon 9 (183 bp). Another mutation shows a partial deletion of exon 10 (63 bp). The fourth mutation consists of a base exchange in exon 8 which disrupts a potential calcium binding site. All of the mutations considered for expression cloning are in the extracellular region of E-cadherin (see FIG. 1 for all mutations).

Starting material for cloning was total RNA isolated from fresh material of diffuse gastric carcinomas in which a respective mutation (see above) was identified. Each of the cDNAs of wild-type E-cadherin and of the mutations obtained after reverse transcription were amplified in the form of two partial fragments (A+B) (see FIG. 7). Taken together, the two partial fragments comprise the complete coding region of E-cadherin consisting of 2649 bp (wild-type). The amplification of fragment A (5' region) was performed using primers ATG and rEX10 (see Table 5). For the amplification of the 3' fragment (B) of the wild-type mRNA, the exon 9 deletion, the partial deletion in exon 10, and the point mutation in exon 8 the pair of primers Ex8-r3'/2/neu was employed. Amplification of fragment B' of the exon 8 deletion mutant was done using the pair Ex 9/1-r3'/2/neu.

The partial fragments A and B amplified were each cloned into PCRII vectors (Invitrogen). Using these vectors a direct and effective cloning of PCR products by means of specific TA base pairing can be achieved. The two partial cDNA fragments of all 5 cadherin cDNAs (wild-type plus 4 mutants) were appropriately joined together by cloning using different cloning strategies which will not be detailed herein but which are well within the skill and the knowledge of one skilled in the art. In this way, constructs of all 5 cDNA in PCRII vectors were obtained.

To exclude cloning artefacts which could have been generated mainly in the course of the amplification (Taq mistakes) all of the 5 cDNAs were examined by sequencing of their full lengths including the vector/cadherin junction regions.

TABLE 5

PCR primers for amplification of E-cadherin and subsequent cloning

| Primer Name | Sequence | Position in E-cadherin mRNA* | SEQ ID NO: |
|---|---|---|---|
| ATG | 5'-ATGGGCCCTT GGAGCCG | 95–111 | 21 |
| Ex 8 | 5'-CTACGTATACC CTGGTGG | 1110–1128 | 22 |
| Ex9/1 | 5'-TACAAGGGTC AGGTGCCTGAG | 1232–1252 | 23 |
| rEx 10 | 5'-GGGGGCTTCAT TCACATC | 1529–1546 | 24 |
| r3'/2/neu | 5'-CCAGCACATG GGTCTGGG | 2764–2781 | 25 |
| Ex7 | 5'-ACCTCTGTGAT GGAGGTC | 929–946 | 26 |
| rEx11 | 5'-TGTGTACGTGC TGTTCTTCACGTG | 1757–1780 | 27 |

*With respect to the E-cadherin sequence Z13009 in the EMBL/GenBank sequence data banks. (The translated reqion extends from nucleotide 95–2743)

In a further step the cadherin constructs verified by sequencing were cloned into eukaryotic expression vectors. On the one hand, the commercially available vector pBK-CMV (Stratagene) which allows for selection of the expressed cellular clones (expression of the neomycin resistance gene) in addition to the expression of the desired cDNA was chosen, on the other hand as a second vector the pBAT vector was used which has already been employed successfully in the transfection of murine wild-type E-cadherin constructs (Nose, A, Nagafuchi, A, Takeichi, M. Expressed recombinant cadherins mediate cell sorting in model systems. Cell 1988; 54:993–1001).

4. Transient Transfection and Detection of E-cadherin by Western-blotting, Immunofluorescence and Immunoelectron Microscopy The $CaPO_4$ precipitation was established for transfection. The transfection efficiency of the method was evaluated using a pCMV plamid (Stratagene) as a control. The vector contains the β-galactosidase gene which allows for detection of the cells having incorporated the vector after conversion of the dye X-Gal (blue stain). The efficiency of the method was in the range of 10% which is a very good value for transient transfections.

In the expression experiments following amplification of the 5' untranslated region which contains the translation recognition region (Kozak sequence) and cloning thereof upstream of the cDNAs it was possible to express the E-cadherin cDNA constructs altered in that manner transiently in MDA-MB-435S cells, MIA PaCa-2, a pancreas cell line deficient for E-cadherin, and in Neuro 2A (neuroblastoma) cells.

The determination of E-cadherin in the cell cultures was done by Western-blotting, immunofluorescence, and immunoelectron microscopy. At first, SDS lysis of the cells (transfected or untransfected) was performed to prepare a whole cell lysate for Western-blotting. Doing this, we obtained an irregular electrophoretic mobility during the subsequent gel run which is neccessary for the examination of the lysate. Alternatively, a cellular extract by Triton X-100 lysis was tested. Examination of the extract by polyacrylamide gel electrophoresis and Coomassie staining showed the disruption of the cells to be effective. Therefore, Triton lysis was used for all subsequent experiments.

We used 4 different monoclonal antibodies against E-cadherin (HECD-1, Takara Biomedicals, Japan; AMST10, Saxon Biomedicals; DECMA-1, Sigma; ANTI-E-CADHERIN, Affinity Research Products Limited) for the specific determination of E-cadherin. The detection of the antigen-antibody complex during Western-blotting was done by a luminescence reaction (ECL-Western, Amersham) using a second peroxidase labeled antibody. Although they reacted with different intensities, all of the antibodies tested showed a specific reaction in the cellular extract with an E-cadherin positive control cell line, A431 (epidermoid carcinoma, ATCC), and with MDA-MB-435S cells transfected by wild-type E-cadherin. No positive signal could be detected in the extracts of the untransfected lines MDA-MB-435S, MIA PaCa-2 and Neuro 2A.

To perform the immunofluorescence, cells seeded onto cover slips were fixed by methanol and labeled by the antibody HECD-1 specific for E-cadherin (recognizes wild-type E-cadherin and mutated, e.g. exon 9 deleted E-cadherin). As a secondary antibody rhodamine- (TRITC-) coupled goat-anti-mouse antibodies (Dianova) were employed.

To determine by means of immunofluorescence whether the transfection had been successful, non-transfected MDA-MB-435S cells, and cells transfected by mutated E-cadherin and by wild-type E-cadherin were examined concurrently. After fixation and incubation with gold-labeled antibody specific for E-cadherin (HECD-1) the labeled cells were embedded in epon and contrasted by uranyl acetate/lead citrate. No labeling could be detected with untransfected MDA-MB-435S cells while the transfected cell lines showed gold labeling associated with the membranes, i.e. wild-type E-cadherin as well as mutated E-cadherin (e.g. having an exon 9 deletion, see FIG. 3) were anchored in the membrane.

5. Cell Lines Stably Expressing E-cadherin

After we were successful in identifying wild-type as well as mutated E-cadherin in transiently transfected cells we started with the preparation of cells stably expressing E-cadherin This was performed by cotransfection of MDA-MB-435S cells with the respective pBAT constructions (see "Cloning") and with pBAT vector without E-cadherin cDNA but instead including the neomycin resistance gene. Three cell lines exhibiting a deletion in exon 9 (Del 9) of the human E-cadherin gene and three lines harboring the wild-type human E-cadherin (WT) were established. Examination of the mRNA by RT-PCR of the Del-9 lines and the WT lines showed the expected fragment sizes (MRNA of normal size for the wild-type (779 bp); shortened mRNA for the Del-9 lines (596 bp), in this case, no wild-type E-cadherin mRNA was expressed!) PCR amplification was carried out using the primers Ex7 and rEX11 (see Table 5). The Western blot of extracts of stably transfected Del-9 lines and of one of the WT lines clearly detected E-cadherin protein.

Examination of the E-cadherin expression in the WT line using immunofluorescence revealed the expected characteristic distribution at the contact sites to the neighbor cell. Using the HECD-1 antibody, the Del-9 cell line also showed labeling of E-cadherin at the cell-to-cell junctions (FIG. 2).

6. Rapid RNA Extraction and Subsequent Determination of the Mutations by PCR (using Peritoneal Lavage as an Example)

Following sedimentation of the cells in the lavage preparation and RNA extraction (Rneasy Rapid extraction Kit, Quiagen) the RNA is reverse transcribed and the full length of the resulting E-cadherin cDNA is amplified by means of PCR (primers and conditions as above). Since the E-cadherin mutations consist mainly of in-frame deletions, these may be quickly and safely detected by agarose gel electropheresis. Thus, already 9 hours after receiving the lavage there may be detected possible deletions in E-cadherin e.g. loss of exon 8 or exon 9, and thereby the detection of disseminated tumor cells in the peritoneal cavity is possible. Due to this information the course of clinical decisions may be directly affected (e.g. additional intraperitoneal therapies).

By this, a highly specific method of detection can be performed rapidly and safely—and also with a low amount of tumor cells. The tumor specificity of the E-cadherin mutations make it possible to exclude ambiguities with respect to cells with "tumor-like" morphology, such as inflammatory mesothelial cell.

7. Preparation and Testing of a Mutation-specific E-cadherin antibody (using antibody 7E6 Specific for the Exon 9 Deletion as an Example)

Peptide synthesis. The following peptide was prepared using a model 430A peptide synthesizer (Applied Biosystems, Foster City, Calif., adapted to Fast-Fmoc modification) (peptide sequence: E-cadherin deletion of exon 9, see Tab. 3 1232del183): Pro-Ile-Phe-Asn-Pro-Thr-Thr-Gly-Leu-Asp-Phe-Glu-Ala (SEQ ID NO:48). The amino acids Asn, Thr, Asp, and Glu were synthesized with protected side chains. The peptide was released off the synthesis resin in 95% trifluoroacetic acid, precipitated by tert butylether and freeze-dried. Afterwards, the raw product was dissolved in 0,1% trifluoroacetic acid and purified using a reverse phase column (Aquapore 300A, C8, Applied Biosystems) with a linear gradient in 70% acetonitrile. The purity of the product was tested in a model AP100 mass spectrometer (Perkin Elmer) by electric spray ionization.

Coupling to a carrier and immunization: keyhole limpet hemocyanin (KLH) from Megathura crenulata (Calbiochem, Bad Soden) was used as a carrier protein for the immunization and was coupled to the peptide in 0.5 M N-methylimidazole buffer (Sigma-Aldrich, Steinheim) pH 7.0 using 1-ethyl-3-(dimethylamino-propyl)carbodiimide at room temperature. In total, 2.8 mg of the peptide were coupled to 2.0 mg of hemocyanin. After dialysis against phosphate-buffered saline (PBS) the resulting solution was used for immunization. The same method was used for the coupling of 2 mg of the peptide to 2 mg of 4× crystallized bovine serum albumine (Behringwerke, Marburg) which was used to test the hybridoma culture supernatants in the ELISA test. The immunization was performed in Lou/C rats, and 50 $\mu$g of KLH-coupled peptide were diluted using 500 $\mu$l PBS and were emulsified by the same amount of CFA. 500 $\mu$l of the resulting emulsion were applied i.p. and s.c., respectively. Three months later a boost injection was performed using KLH-coupled peptide but without CFA. The fusion was carried out 3 days after boost injection. The murine plasmocytoma cell line P3×63 Ag 8.653 served as fusion cell line. An ELISA was performed to test for the specific peptide and for an irrelevant peptide coupled to BSA using identical coupling chemistry which served as a control. Hybridomas reacting exclusively with the specific peptide were frozen, and the supernatants thereof were subjected to further analysis. Subclasses were determined using subclass-specific monoclonal antibodies.

FACS analysis: 200.000 MDA-MB-435S cells transfected with exon 9 deleted E-cadherin (see above) or 200.000 untransfected MDA-MB-435S cells, respectively, were incubated together with 50 $\mu$l of hybridoma supernatant. 50 $\mu$l of suitably diluted goat-anti-rat FITC were added for 30 min to detect the bound antibodies. The cells were analysed in the FACscan (Becton). The mab 7E6 belongs to the "rat IgG1" subclass and shows the highest intensity in the FACscan.

Immunofluorescence: To perform the immunofluorescence, the cells seeded on cover slips (MDA-MB-435S cells transfected by exon 9 deleted E-cadherin or untransfected MDA-MB-435S cells, respectively) were fixed with methanol and labeled by antibody 7E6 specific for E-cadherin mutations. As a secondary antibody, FITC-coupled goat-anti-rat antibody (Dianova) was used.

Western-blotting: Cellular extracts of E-cadherin transfected MDA-MB-435S cells (transfected either with wild-type or exon 9 deleted E-cadherin) and of additional cell lines were examined by the mutation-specific antibody 7E6 on a Western blot. Using the antibody 7E6 no positive signal could be detected in the extracts of the untransfected lines MDA-MB-435S, MIA PaCa-2 (human pancreatic carcinoma), Neuro 2A, and A431 (epidermoid carcinoma, ATCC). Also, the cells transfected by wild-type E-cadherin failed to show a signal with 7E6. The only cell line which had reacted with the mutation-specific E-cadherin antibody 7E6 was MDA-MB-435S which had been transfected by exon 9 deleted E-cadherin.

Immunohistochemistry: Archive marterial (formalin-fixed and paraffin-embedded tissue) of gastric carcinoma patients in which the loss of exon 9 of E-cadherin had been detected by molecular biology was subjected to deparaffinization and rehydration. After treatment with citric acid and microwaves the tissue samples were incubated for 15 minutes in 1% $H_2O_2$ to block the endogenous peroxidase. For the detection of E-cadherin mutation-specific immunoreactivity the tissues were incubated with 7E6 monoclonal antibody at 40° C. over 16 hours. Binding of the antibody was visualized using avidin-biotin complex (ABC) and the peroxidase method (ABC Elite Kit, Vector, Burlingame, Calif.; Sigma Fast DAB, Sigma, Deisenhofen). Counterstaining of the nucleus was performed using hemalum. All of the tumor sections also showed portions of non-malignant mucosa as a control. Negative controls were carried out substituting the 7E6 antibody by phosphate-buffered NaCl.

What is claimed is:

1. Monoclonal antibody specifically directed against amino acid sequences of mutated E-cadherin, which E-cadherin is localized in the cell membrane, and which amino acid sequences of mutated E-cadherin have been generated by in-frame mutations on the DNA level, characterized in that said antibody recognizes a sequence region selected from the group consisting of the following amino acid sequences which have been generated by deletion or amino acid exchange as compared to wild-type E-cadherin:

| Mutation | Mutated E-cadherin sequence | SEQ ID NO: |
| --- | --- | --- |
| 563del63 | PGLRRQKRDW/IKSNKDKEGK | SEQ ID NO:2 |
| 706del9 | QGADTPPVGV/ERETGQLKVT | SEQ ID NO:4 |
| 1036del115 | LSQDPELPDK/NRNTGFVISVV | SEQ ID NO:6 |
| 1103del129 | SVVTRTGLDRE/YKGQVPENEA | SEQ ID NO:8 |
| 1232del183 | DNPPIFNPTT/GLDFEAKQQY | SEQ ID NO:10 |
| 1414del169 | NNDGILKTAK/VSLTTSTATV | SEQ ID NO:12 |
| Asp370Ala | TAVITVTDTNANPPIFNPTT | SEQ ID NO:16 |
| Arg598Gln | VNDNAPIPEPQTIFFCERNP | SEQ ID NO:18 |
| 826del9 | AVSSNGNAVEE/ILITVTDQN | SEQ ID NO:20 | wherein "/" denotes the position of a deletion, and bold letters denote amino acids changed by point mutations, respectively, each in comparison to the wild-type E-cadherin protein.

2. Mixture of at least two monoclonal antibodies being specifically directed against at least one of the amino acid sequences of claim 1.

3. Cell line producing monoclonal antibodies specifically directed against amino acid sequences of mutated E-cadherin, characterized in that
said cell line is the hybridoma cell line delta CAD-9, clone 7E6-1, deposition No. DSM ACC 2277.

* * * * *

UNITED STATES PATENT AND TRADEMARK OFFICE
CERTIFICATE OF CORRECTION

PATENT NO.    : 6,447,776 B1                                    Page 1 of 1
DATED         : September 10, 2002
INVENTOR(S)   : Höfler et al.

It is certified that error appears in the above-identified patent and that said Letters Patent is hereby corrected as shown below:

<u>Column 45, line 24 through Column 46, line 16,</u>
Delete the table and insert therefore the following table:

| -- Mutation | Mutated E-cadherin sequence | SEQ ID NO: |
|---|---|---|
| 563del63 | PGLRRQKRDW/IKSNKDKEGK | SEQ ID NO:2 |
| 706del9 | QGADTPPVGV/ERETGWLKVT | SEQ ID NO:4 |
| 1036del15 | LSQDPELPDK/NRNTGVISVV | SEQ ID NO:6 |
| 1103del129 | SVVTTGLDRE/YKGQVPENEA | SEQ ID NO:8 |
| 1232del183 | DNPPIFNPTT/GLDFEAKQQY | SEQ ID NO:10 |
| 1414del69 | NNDGILKTAK/VSLTTSTATV | SEQ ID NO:12 |
| Asp370Ala | TAVITVTDTNANPPIFNPTT | SEQ ID NO:14 |
| Val473Asp | EVSLTTSTATDTVDVLDVNE | SEQ ID NO:16 |
| Arg598Gln | VNDNAPIPEPQTIFFCERNP | SEQ ID NO:18 |
| 826del9 | AVSSNGNAVEE/ILITVTDQN | SEQ ID NO:20 -- |

Signed and Sealed this

Seventeenth Day of February, 2004

JON W. DUDAS
*Acting Director of the United States Patent and Trademark Office*

```
                          SEQUENCE LISTING (1) GENERAL INFORMATION:

(iii) NUMBER OF SEQUENCES: 48

(2) INFORMATION FOR SEQ ID NO:1:

(i) SEQUENCE CHARACTERISTICS:
         (A) LENGTH: 20 amino acids
         (B) TYPE: amino acid
         (C) STRANDEDNESS:
         (D) TOPOLOGY: linear (ii) MOLECULE TYPE: peptide (ix) FEATURE:
         (A) NAME/KEY: Peptide
         (B) LOCATION: 1..20
         (D) OTHER INFORMATION: /note= "amino acid sequence translated
             from nucleotides at positions 534 through 593 in "normal"
             human E-cadherin cDNA"

(xi) SEQUENCE DESCRIPTION: SEQ ID NO:1:

Pro Gly Leu Arg Arg Gln Lys Arg Asp Trp Val Ile Pro Pro Ile Ser
1               5                  10                  15

Cys Pro Glu Asn
            20

(2) INFORMATION FOR SEQ ID NO:2:

(i) SEQUENCE CHARACTERISTICS:
         (A) LENGTH: 20 amino acids
         (B) TYPE: amino acid
         (C) STRANDEDNESS:
         (D) TOPOLOGY: linear (ii) MOLECULE TYPE: peptide (ix) FEATURE:
         (A) NAME/KEY: Peptide
         (B) LOCATION: 20
         (D) OTHER INFORMATION: /note= "amino acid sequence generated
             by the 563del63 mutation in the human E-cadherin gene"

(xi) SEQUENCE DESCRIPTION: SEQ ID NO:2:

Pro Gly Leu Arg Arg Gln Lys Arg Asp Trp Ile Lys Ser Asn Lys Asp
1               5                  10                  15

Lys Glu Gly Lys
            20

(2) INFORMATION FOR SEQ ID NO:3:

(i) SEQUENCE CHARACTERISTICS:
         (A) LENGTH: 20 amino acids
         (B) TYPE: amino acid
         (C) STRANDEDNESS:
         (D) TOPOLOGY: linear (ii) MOLECULE TYPE: peptide
```

(ix) FEATURE:
    (A) NAME/KEY: Peptide
    (B) LOCATION: 1..20
    (D) OTHER INFORMATION: /note= "amino acid sequence translated
        from nucleotides at positions 678 through 737 of "normal"
        human E-cadherin cDNA"

(xi) SEQUENCE DESCRIPTION: SEQ ID NO:3:

Gln Gly Ala Asp Thr Pro Pro Val Gly Val Phe Ile Ile Glu Arg Glu
1               5                   10                  15

Thr Gly Trp Leu
            20

(2) INFORMATION FOR SEQ ID NO:4:

(i) SEQUENCE CHARACTERISTICS:
        (A) LENGTH: 20 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Peptide
        (B) LOCATION: 1..20
        (D) OTHER INFORMATION: /note= "amino acid sequence generated
            by the 706del9 mutation in the human E-cadherin gene"

(xi) SEQUENCE DESCRIPTION: SEQ ID NO:4:

Gln Gly Ala Asp Thr Pro Pro Val Gly Val Glu Arg Glu Thr Gly Trp
1               5                   10                  15

Leu Lys Val Thr
            20

(2) INFORMATION FOR SEQ ID NO:5:

(i) SEQUENCE CHARACTERISTICS:
        (A) LENGTH: 20 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Peptide
        (B) LOCATION: 1..20
        (D) OTHER INFORMATION: /note= "amino acid sequence translate
            from nucleotides at positions 1007 through 1066 of
            "normal" human E-cadherin cDNA"

(xi) SEQUENCE DESCRIPTION: SEQ ID NO:5:

Leu Ser Gln Asp Pro Glu Leu Pro Asp Lys Asn Met Phe Thr Ile Asn
1               5                   10                  15

Arg Asn Thr Gly
            20

(2) INFORMATION FOR SEQ ID NO:6:

(i) SEQUENCE CHARACTERISTICS:
        (A) LENGTH: 20 amino acids
        (B) TYPE: amino acid
        (C) STRANDEDNESS:
        (D) TOPOLOGY: linear (ii) MOLECULE TYPE: peptide (ix) FEATURE:

```
        (A) NAME/KEY: Peptide
        (B) LOCATION: 1..20
        (D) OTHER INFORMATION: /note= "amino acid sequence generated
            by the 1036del15 mutation in the human E-cadherin gene"

(xi) SEQUENCE DESCRIPTION: SEQ ID NO:6:

Leu Ser Gln Asp Pro Glu Leu Pro Asp Lys Asn Arg Asn Thr Gly Val
1               5                   10                  15

Ile Ser Val Val
            20

(2) INFORMATION FOR SEQ ID NO:7:

(i) SEQUENCE CHARACTERISTICS:
        (A) LENGTH: 20 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Peptide
        (B) LOCATION: 20
        (D) OTHER INFORMATION: /note= "amino acid sequence translated
            from nucleotides at positions 1074 through 1133 of
            "normal" human E-cadherin cDNA"

(xi) SEQUENCE DESCRIPTION: SEQ ID NO:7:

Ser Val Val Thr Thr Gly Leu Asp Arg Glu Ser Phe Pro Thr Tyr Thr
1               5                   10                  15

Leu Val Val Gln
            20

(2) INFORMATION FOR SEQ ID NO:8:

(i) SEQUENCE CHARACTERISTICS:
        (A) LENGTH: 20 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Peptide
        (B) LOCATION: 1..20
        (D) OTHER INFORMATION: /note= "amino acid sequence generated
            by the 1103del129 mutation in the human E-cadherin gene"

(xi) SEQUENCE DESCRIPTION: SEQ ID NO:8:

Ser Val Val Thr Thr Gly Leu Asp Arg Glu Tyr Lys Gly Gln Val Pro
1               5                   10                  15

Glu Asn Glu Ala
            20

(2) INFORMATION FOR SEQ ID NO:9:

(i) SEQUENCE CHARACTERISTICS:
        (A) LENGTH: 20 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Peptide
        (B) LOCATION: 1..20
        (D) OTHER INFORMATION: /note= "amino acid sequence translated
``` from nucleotides at positions 1203 through 1262 of
"normal" human E-cadherin cDNA"

(xi) SEQUENCE DESCRIPTION: SEQ ID NO:9:

Asp Asn Pro Pro Ile Phe Asn Pro Thr Thr Tyr Lys Gly Gln Val Pro
1               5                   10                  15

Glu Asn Glu Ala
            20

(2) INFORMATION FOR SEQ ID NO:10:

(i) SEQUENCE CHARACTERISTICS:
       (A) LENGTH: 20 amino acids
       (B) TYPE: amino acid
       (C) STRANDEDNESS:
       (D) TOPOLOGY: linear (ii) MOLECULE TYPE: peptide (ix) FEATURE:
       (A) NAME/KEY: Peptide
       (B) LOCATION: 1..20
       (D) OTHER INFORMATION: /note= "amino acid sequence generated
           by the 1232del183 mutation in the human E-cadherin gene"

(xi) SEQUENCE DESCRIPTION: SEQ ID NO:10:

Asp Asn Pro Pro Ile Phe Asn Pro Thr Thr Gly Leu Asp Phe Glu Ala
1               5                   10                  15

Lys Gln Gln Tyr
            20

(2) INFORMATION FOR SEQ ID NO:11:

(i) SEQUENCE CHARACTERISTICS:
       (A) LENGTH: 20 amino acids
       (B) TYPE: amino acid
       (C) STRANDEDNESS:
       (D) TOPOLOGY: linear (ii) MOLECULE TYPE: peptide (ix) FEATURE:
       (A) NAME/KEY: Peptide
       (B) LOCATION: 1..20
       (D) OTHER INFORMATION: /note= "amino acid sequence translated
           from nucleotides at positions 1385 through 1444 of
           "normal" human E-cadherin"

(xi) SEQUENCE DESCRIPTION: SEQ ID NO:11:

Asn Asn Asp Gly Ile Leu Lys Thr Ala Lys Gly Leu Asp Phe Glu Ala
1               5                   10                  15

Lys Gln Gln Tyr
            20

(2) INFORMATION FOR SEQ ID NO:12:

(i) SEQUENCE CHARACTERISTICS:
       (A) LENGTH: 20 amino acids
       (B) TYPE: amino acid
       (C) STRANDEDNESS:
       (D) TOPOLOGY: linear (ii) MOLECULE TYPE: peptide (ix) FEATURE:
       (A) NAME/KEY: Peptide
       (B) LOCATION: 1..20
       (D) OTHER INFORMATION: /note= "amino acid sequence generated
           by the 1414del69 mutation in the human E-cadherin gene"

(xi) SEQUENCE DESCRIPTION: SEQ ID NO:12:

Asn Asn Asp Gly Ile Leu Lys Thr Ala Lys Val Ser Leu Thr Thr Ser
1               5                  10                  15

Thr Ala Thr Val
            20

(2) INFORMATION FOR SEQ ID NO:13:

(i) SEQUENCE CHARACTERISTICS:
        (A) LENGTH: 20 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Peptide
        (B) LOCATION: 1..20
        (D) OTHER INFORMATION: /note= "amino acid sequence at
            positions 360 through 379 of "normal" human E-cadherin
            protein"

(xi) SEQUENCE DESCRIPTION: SEQ ID NO:13:

Thr Ala Val Ile Thr Val Thr Asp Thr Asn Asp Asn Pro Pro Ile Phe
1               5                  10                  15

Asn Pro Thr Thr
            20

(2) INFORMATION FOR SEQ ID NO:14:

(i) SEQUENCE CHARACTERISTICS:
        (A) LENGTH: 20 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Peptide
        (B) LOCATION: 1..20
        (D) OTHER INFORMATION: /note= "amino acid sequence generated
            by the Asp370Ala mutation in human E-cadherin protein"

(xi) SEQUENCE DESCRIPTION: SEQ ID NO:14:

Thr Ala Val Ile Thr Val Thr Asp Thr Asn Ala Asn Pro Pro Ile Phe
1               5                  10                  15

Asn Pro Thr Thr
            20

(2) INFORMATION FOR SEQ ID NO:15:

(i) SEQUENCE CHARACTERISTICS:
        (A) LENGTH: 20 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Peptide
        (B) LOCATION: 1..20
        (D) OTHER INFORMATION: /note= "amino acid sequence at
            positions 463 through 482 of "normal" human E-cadherin
            protein"

(xi) SEQUENCE DESCRIPTION: SEQ ID NO:15:

```
Glu Val Ser Leu Thr Thr Ser Thr Ala Thr Val Thr Val Asp Val Leu
1               5                   10                  15

Asp Val Asn Glu
            20
```

(2) INFORMATION FOR SEQ ID NO:16:

(i) SEQUENCE CHARACTERISTICS:
        (A) LENGTH: 20 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Peptide
        (B) LOCATION: 1..20
        (D) OTHER INFORMATION: /note= "amino acid sequence generated
            by the Val473Asp mutation in human E-cadherin protein"

(xi) SEQUENCE DESCRIPTION: SEQ ID NO:16:

```
Glu Val Ser Leu Thr Thr Ser Thr Ala Thr Asp Thr Val Asp Val Leu
1               5                   10                  15

Asp Val Asn Glu
            20
```

(2) INFORMATION FOR SEQ ID NO:17:

(i) SEQUENCE CHARACTERISTICS:
        (A) LENGTH: 20 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Peptide
        (B) LOCATION: 1..20
        (D) OTHER INFORMATION: /note= "amino acid sequence at
            positions 588 through 607 of "normal" human E-cadherin
            protein"

(xi) SEQUENCE DESCRIPTION: SEQ ID NO:17:

```
Val Asn Asp Asn Ala Pro Ile Pro Glu Pro Arg Thr Ile Phe Phe Cys
1               5                   10                  15

Glu Arg Asn Pro
            20
```

(2) INFORMATION FOR SEQ ID NO:18:

(i) SEQUENCE CHARACTERISTICS:
        (A) LENGTH: 20 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Peptide
        (B) LOCATION: 1..20
        (D) OTHER INFORMATION: /note= "amino acid sequence
            generated by the Arg598Gln mutation in human E-cadherin
            protein"

(xi) SEQUENCE DESCRIPTION: SEQ ID NO:18:

```
Val Asn Asp Asn Ala Pro Ile Pro Glu Pro Gln Thr Ile Phe Phe Cys
1               5                   10                  15
```

Glu Arg Asn Pro
        20

(2) INFORMATION FOR SEQ ID NO:19:

(i) SEQUENCE CHARACTERISTICS:
        (A) LENGTH: 19 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Peptide
        (B) LOCATION: 1..19
        (D) OTHER INFORMATION: /note= "amino acid sequence
            translated from nucleotides at positions 795 through 854
            of "normal" human E-cadherin cDNA"

(xi) SEQUENCE DESCRIPTION: SEQ ID NO:19:

Ala Val Ser Ser Asn Gly Asn Ala Val Glu Asp Pro Met Glu Ile Leu
1               5                   10                  15

Ile Thr Val (2) INFORMATION FOR SEQ ID NO:20:

(i) SEQUENCE CHARACTERISTICS:
        (A) LENGTH: 20 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Peptide
        (B) LOCATION: 1..20
        (D) OTHER INFORMATION: /note= "amino acid sequence
            generated by the 826del9 mutation in the human E-cadherin
            gene"

(xi) SEQUENCE DESCRIPTION: SEQ ID NO:20:

Ala Val Ser Ser Asn Gly Asn Ala Val Glu Glu Ile Leu Ile Thr Val
1               5                   10                  15

Thr Asp Gln Asn
        20

(2) INFORMATION FOR SEQ ID NO:21:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..17
        (D) OTHER INFORMATION: /note= "primer ATG"

(xi) SEQUENCE DESCRIPTION: SEQ ID NO:21:

ATGGGCCCTT GGAGCCG                                                          17

(2) INFORMATION FOR SEQ ID NO:22:

(i) SEQUENCE CHARACTERISTICS:

(A) LENGTH: 18 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..18
        (D) OTHER INFORMATION: /note= "primer Ex 8"

(xi) SEQUENCE DESCRIPTION: SEQ ID NO:22:

CTACGTATAC CCTGGTGG                                                18

(2) INFORMATION FOR SEQ ID NO:23:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..21
        (D) OTHER INFORMATION: /note= "primer Ex9/1"

(xi) SEQUENCE DESCRIPTION: SEQ ID NO:23:

TACAAGGGTC AGGTGCCTGA G                                            21

(2) INFORMATION FOR SEQ ID NO:24:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..18
        (D) OTHER INFORMATION: /note= "primer rEx 10"

(xi) SEQUENCE DESCRIPTION: SEQ ID NO:24:

GGGGGCTTCA TTCACATC                                                18

(2) INFORMATION FOR SEQ ID NO:25:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..18
        (D) OTHER INFORMATION: /note= "primer r3'/2/neu"

(xi) SEQUENCE DESCRIPTION: SEQ ID NO:25:

CCAGCACATG GGTCTGGG                                                18

(2) INFORMATION FOR SEQ ID NO:26:

```
          (i) SEQUENCE CHARACTERISTICS:
              (A) LENGTH: 18 base pairs
              (B) TYPE: nucleic acid
              (C) STRANDEDNESS: single
              (D) TOPOLOGY: linear (ii) MOLECULE TYPE: DNA (ix) FEATURE:
              (A) NAME/KEY: -
              (B) LOCATION: 1..18
              (D) OTHER INFORMATION: /note= "primer Ex7"

(xi) SEQUENCE DESCRIPTION: SEQ ID NO:26:

ACCTCTGTGA TGGAGGTC                                                    18

(2) INFORMATION FOR SEQ ID NO:27:

(i) SEQUENCE CHARACTERISTICS:
              (A) LENGTH: 24 base pairs
              (B) TYPE: nucleic acid
              (C) STRANDEDNESS: single
              (D) TOPOLOGY: linear (ii) MOLECULE TYPE: DNA (ix) FEATURE:
              (A) NAME/KEY: -
              (B) LOCATION: 1..24
              (D) OTHER INFORMATION: /note= "primer rEx11"

(xi) SEQUENCE DESCRIPTION: SEQ ID NO:27:

TGTGTACGTG CTGTTCTTCA CGTG                                             24

(2) INFORMATION FOR SEQ ID NO:28:

(i) SEQUENCE CHARACTERISTICS:
              (A) LENGTH: 20 base pairs
              (B) TYPE: nucleic acid
              (C) STRANDEDNESS: single
              (D) TOPOLOGY: linear (ii) MOLECULE TYPE: DNA (ix) FEATURE:
              (A) NAME/KEY: -
              (B) LOCATION: 1..20
              (D) OTHER INFORMATION: /note= ""forward" primer ATG"

(xi) SEQUENCE DESCRIPTION: SEQ ID NO:28:

CCATGGGCCC TTGGAGCCGC                                                  20

(2) INFORMATION FOR SEQ ID NO:29:

(i) SEQUENCE CHARACTERISTICS:
              (A) LENGTH: 22 base pairs
              (B) TYPE: nucleic acid
              (C) STRANDEDNESS: single
              (D) TOPOLOGY: linear (ii) MOLECULE TYPE: DNA (ix) FEATURE:
              (A) NAME/KEY: -
              (B) LOCATION: 1..22
              (D) OTHER INFORMATION: /note= ""reverse" primer rEx6"

(xi) SEQUENCE DESCRIPTION: SEQ ID NO:29:

CTGGAAGAGC ACCTTCCATG AC                                               22

(2) INFORMATION FOR SEQ ID NO:30:
```

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: DNA (ix) FEATURE:
            (A) NAME/KEY: -
            (B) LOCATION: 1..24
            (D) OTHER INFORMATION: /note= ""forward" primer Ex5"

(xi) SEQUENCE DESCRIPTION: SEQ ID NO:30:

ACAGAGCCTC TGGATAGAGA ACGC                                          24

(2) INFORMATION FOR SEQ ID NO:31:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (ix) FEATURE:
            (A) NAME/KEY: -
            (B) LOCATION: 1..20
            (D) OTHER INFORMATION: /note= ""reverse" primer rEx10/2"

(xi) SEQUENCE DESCRIPTION: SEQ ID NO:31:

CCACATTCGT CACTGCTACG                                               20

(2) INFORMATION FOR SEQ ID NO:32:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: DNA (ix) FEATURE:
            (A) NAME/KEY: -
            (B) LOCATION: 1..22
            (D) OTHER INFORMATION: /note= ""forward" primer Ex9/2a"

(xi) SEQUENCE DESCRIPTION: SEQ ID NO:32:

CAGCGTGGGA GGCTGTATAC AC                                            22

(2) INFORMATION FOR SEQ ID NO:33:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: DNA (ix) FEATURE:
            (A) NAME/KEY: -
            (B) LOCATION: 1..21
            (D) OTHER INFORMATION: /note= ""reverse" primer rEx11"

(xi) SEQUENCE DESCRIPTION: SEQ ID NO:33:

TGTGTACGTG CTGTTCTTCA C                                             21

(2) INFORMATION FOR SEQ ID NO:34:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..21
        (D) OTHER INFORMATION: /note= ""forward" primer Ex10/2"

(xi) SEQUENCE DESCRIPTION: SEQ ID NO:34:

GTGTCCGAGG ACTTTGGCGT G                                      21

(2) INFORMATION FOR SEQ ID NO:35:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..25
        (D) OTHER INFORMATION: /note= ""reverse" primer rEx13"

(xi) SEQUENCE DESCRIPTION: SEQ ID NO:35:

TCAGAATTAG CAAAGCAAGA ATTCC                                25

(2) INFORMATION FOR SEQ ID NO:36:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..21
        (D) OTHER INFORMATION: /note= ""forward" primer Ex13"

(xi) SEQUENCE DESCRIPTION: SEQ ID NO:36:

GGCGTCTGTA GGAAGGCACA G                                      21

(2) INFORMATION FOR SEQ ID NO:37:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..18
        (D) OTHER INFORMATION: /note= ""reverse" primer r3prime"

(xi) SEQUENCE DESCRIPTION: SEQ ID NO:37:

CCAGCACATG GGTCTGGG                                              18

(2) INFORMATION FOR SEQ ID NO:38:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..60
        (D) OTHER INFORMATION: /note= "sequence region generated by
           mutation 563del63"

(xi) SEQUENCE DESCRIPTION: SEQ ID NO:38:

```
CCTGGCCTCA GAAGACAGAA GAGAGACTGG ATCAAATCCA ACAAAGACAA AGAAGGCAAG      60
```

(2) INFORMATION FOR SEQ ID NO:39:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..60
        (D) OTHER INFORMATION: /note= "sequence region generated by
           mutation 706del9"

(xi) SEQUENCE DESCRIPTION: SEQ ID NO:39:

```
CAAGGAGCTG ACACACCCCC TGTTGGTGTT GAAAGAGAAA CAGGATGGCT GAAGGTGACA      60
```

(2) INFORMATION FOR SEQ ID NO:40:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..60
        (D) OTHER INFORMATION: /note= "sequence region generated by
           mutation 1036del15"

(xi) SEQUENCE DESCRIPTION: SEQ ID NO:40:

```
CTCAGCCAAG ATCCTGAGCT CCCTGACAAA AACAGGAACA CAGGAGTCAT CAGTGTGGTC      60
```

(2) INFORMATION FOR SEQ ID NO:41:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..60
        (D) OTHER INFORMATION: /note= "sequence region generated by
           mutation 1103del129"

(xi) SEQUENCE DESCRIPTION: SEQ ID NO:41:

AGTGTGGTCA CCACTGGGCT GGACCGAGAG TACAAGGGTC AGGTGCCTGA GAACGAGGCT    60

(2) INFORMATION FOR SEQ ID NO:42:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..60
        (D) OTHER INFORMATION: /note= "sequence region generated by
            mutation 1232del183"

(xi) SEQUENCE DESCRIPTION: SEQ ID NO:42:

GATAATCCTC CGATCTTCAA TCCCACCACG GGCTTGGATT TTGAGGCCAA GCAGCAGTAC    60

(2) INFORMATION FOR SEQ ID NO:43:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..60
        (D) OTHER INFORMATION: /note= "sequence region generated by
            mutation 1414del69"

(xi) SEQUENCE DESCRIPTION: SEQ ID NO:43:

AACAACGATG GCATTTTGAA AACAGCAAAG GTNTCTCTCA CCACCTCCAC AGCCACCGTC    60

(2) INFORMATION FOR SEQ ID NO:44:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..60
        (D) OTHER INFORMATION: /note= "sequence region generated by
            mutation Asp370Ala"

(xi) SEQUENCE DESCRIPTION: SEQ ID NO:44:

ACAGCTGTGA TCACAGTCAC TGACACCAAC GCTAATCCTC CGATCTTCAA TCCCACCACG    60

(2) INFORMATION FOR SEQ ID NO:45:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ii) MOLECULE TYPE: DNA (ix) FEATURE:
              (A) NAME/KEY: -
              (B) LOCATION: 1..60
              (D) OTHER INFORMATION: /note= "sequence region generated by
                  mutation Val473Asp"

(xi) SEQUENCE DESCRIPTION: SEQ ID NO:45:

GAGGTCTCTC TCACCACCTC CACAGCCACC GACACCGTGG ATGTGCTGGA TGTGAATGAA        60

(2) INFORMATION FOR SEQ ID NO:46:

(i) SEQUENCE CHARACTERISTICS:
              (A) LENGTH: 60 base pairs
              (B) TYPE: nucleic acid
              (C) STRANDEDNESS: single
              (D) TOPOLOGY: linear (ii) MOLECULE TYPE: DNA (ix) FEATURE:
              (A) NAME/KEY: -
              (B) LOCATION: 1..60
              (D) OTHER INFORMATION: /note= "sequence region generated by
                  mutation Arg598Gln"

(xi) SEQUENCE DESCRIPTION: SEQ ID NO:46:

GTGAATGACA ACGCCCCCAT ACCAGAACCT CAAACTATAT TCTTCTGTGA GAGGAATCCA        60

(2) INFORMATION FOR SEQ ID NO:47:

(i) SEQUENCE CHARACTERISTICS:
              (A) LENGTH: 60 base pairs
              (B) TYPE: nucleic acid
              (C) STRANDEDNESS: single
              (D) TOPOLOGY: linear (ii) MOLECULE TYPE: DNA (ix) FEATURE:
              (A) NAME/KEY: -
              (B) LOCATION: 1..60
              (D) OTHER INFORMATION: /note= "sequence region generated by
                  mutation 826del9"

(xi) SEQUENCE DESCRIPTION: SEQ ID NO:47:

GCTGTGTCAT CCAACGGGAA TGCAGTTGAG GAGATTTTGA TCACGGTAAC CGATCAGAAT        60

(2) INFORMATION FOR SEQ ID NO:48:

(i) SEQUENCE CHARACTERISTICS:
              (A) LENGTH: 13 amino acids
              (B) TYPE: amino acid
              (C) STRANDEDNESS:
              (D) TOPOLOGY: linear (ii) MOLECULE TYPE: peptide (ix) FEATURE:
              (A) NAME/KEY: Peptide
              (B) LOCATION: 1..13
              (D) OTHER INFORMATION: /note= "amino acid sequence generated
                  by the mutation 1232del183 in the human E-cadherin gene"

(xi) SEQUENCE DESCRIPTION: SEQ ID NO:48:

Pro Ile Phe Asn Pro Thr Thr Gly Leu Asp Phe Glu Ala
1               5                   10